United States Patent [19]

Miller et al.

[11] Patent Number: 5,423,820
[45] Date of Patent: Jun. 13, 1995

[54] SURGICAL CABLE AND CRIMP

[75] Inventors: David F. Miller; Robert A. Farris, both of Memphis; Bradley J. Coates, Cordova, all of Tenn.

[73] Assignee: Danek Medical, Inc., Memphis, Tenn.

[21] Appl. No.: 95,146

[22] Filed: Jul. 20, 1993

[51] Int. Cl.⁶ .............................................. A61B 17/58
[52] U.S. Cl. ................... 606/74; 24/129 W; 29/282; 29/283.5
[58] Field of Search ............ 606/60, 86, 103, 232, 606/157, 158, 74; 24/22, 23 W, 115 A, 129 W; 29/282, 283.5; 140/123.5, 123.6

[56] References Cited

U.S. PATENT DOCUMENTS

| | | | |
|---|---|---|---|
| 3,802,438 | 4/1974 | Wolvek | 606/232 |
| 3,840,018 | 10/1974 | Heifetz | 606/158 |
| 4,128,100 | 12/1978 | Wendorff | 606/74 |
| 4,889,110 | 12/1989 | Galline et al. | |
| 4,966,600 | 10/1990 | Songer et al. | |
| 5,116,340 | 5/1989 | Songer et al. | |
| 5,123,456 | 6/1992 | Jansen | 140/123.6 |
| 5,312,410 | 5/1994 | Miller et al. | 606/103 |

FOREIGN PATENT DOCUMENTS 2911748  10/1980  Germany ................ 606/74

*Primary Examiner*—Tamara L. Graysay
*Attorney, Agent, or Firm*—Woodard, Emhardt, Naughton, Moriarty & McNett

[57] ABSTRACT

A double-apertured L-shaped crimp is crimped to one end of a cable. The other end of the cable is passed around the bone or bones and, if the situation requires, any orthopedic appliance or device to be attached to the bones, and it is then passed through the other aperture in the crimp. The cable is then tensioned by application thereto of a tensioning tool with the tool applied to the cable and to an abutment face of the crimp, whereupon the cable is tensioned. Then the cable portion in the aperture adjacent the tensioning tool is crimped onto the cable to complete the attachment. Then the tensioning tool is removed, and the free end of the cable is cut off at the abutment surface.

6 Claims, 3 Drawing Sheets

SURGICAL CABLE AND CRIMP

BACKGROUND OF THE INVENTION

1. Field of the Invention

This invention relates generally to orthopedics and spinal surgery, and more particularly to a method and apparatus for securing cable to bone.

2. Description of the Prior Art

Many ways and means have been developed for securing bone in place and for securing devices to bone. While single filament wires were used for many years in various types of surgical procedures, multi-filament cables have been used increasingly in recent years, particularly where strength and long-term reliability in a comparatively inaccessible site, are important. One example is shown in U.S. Pat. No. 4,889,110 issued Dec. 26, 1989 to Galline et al. In that example, an anchoring plate 11 has four bores therein receiving two crimping tubes and two crimping rings for holding multi-ply cables to secure a trochanter major to the femur. Another example of use of multi-filament cables is shown in U.S. Pat. Nos. 5,116,340 and 4,966,600 to Songer et al. Both Songer et al. patents use a loop 38 and a flanged tube crimp member 28 as in FIG. 1, of these Patents or a stop member 94, bar 96 and a crimp member having a front flange 60 as in FIG. 6, of those Patents to secure the cable. Because of the need to minimize space requirements for cabling, crimp members of the type shown in the Songer patents are small. As a result, they are difficult to handle, cannot be manipulated well with surgical gloves, and can be dropped easily. It is desirable to provide a system whereby a separate loose crimp is not needed, the crimp is reliably secured and securable to the cable, does not require tight bends or small loops in the cable, and which does not require cable-to-cable contact stress as in the cable passing through the small loop 38 in the FIG. 1 embodiment of the Songer patents.

SUMMARY OF THE INVENTION

Described briefly according to a typical embodiment of the present invention, a double-apertured crimp is crimped to one end of a cable. The other end of the cable is passed around the bone or bones and, if the situation requires, any orthopedic appliance or device to be attached to the bones, and it is then passed through the other aperture in the crimp. The cable is then tensioned by application thereto of a tensioning tool with the tool applied to the cable and to an abutment face of the crimp, whereupon the cable is tensioned. Then the cable portion in the aperture adjacent the tensioning tool is secured in the crimp by swaging the crimp onto the cable to complete the attachment. Then the tensioning tool is removed, and the free end of the cable is cut off at the abutment surface.

DESCRIPTION OF THE PREFERRED EMBODIMENT

Figure 1:
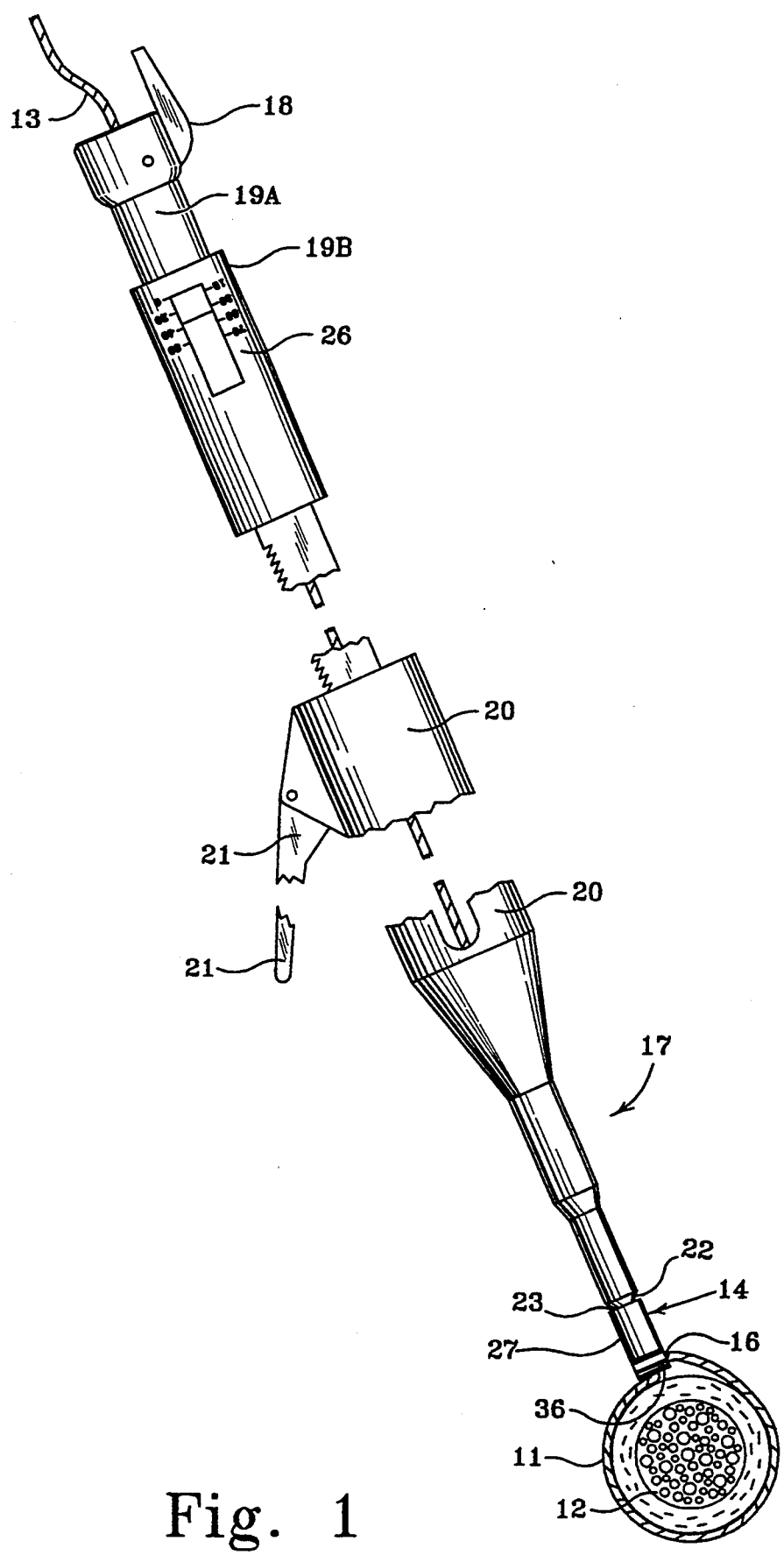
FIG. 1 is a schematic illustration of the application of the crimp assembly to a bone.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, and more particularly FIG. 1, the goal is to secure cable 11 around bone 12, with the proper tension on the cable, and maintain it. For that purpose, the free end 13 of the cable is passed around the bone 12 while the crimp 14 at the other end 16 of the cable is held at a suitable location above the bone. Then the free end 13 is passed up through an aperture in the crimp and then through the central passageway in a tensioning tool 17. Then a clamp lug 18 at the upper end of the tool 17 clamps a portion 19A of the tensioning tool onto the cable. Portion 19A telescopes within portion 19B which is secured to a bar which telescopes into the barrel 20 of the tensioning tool and, upon operation of the hand lever 21, portion 19B is ratcheted out of the barrel 20 whereupon the barrel tip 22 abuttingly engages the tool receiving abutment end 23 of the crimp 14. Further ratcheting of the tool pulls the cable up through the aperture 24 in the crimp 14 until the desired tension is reached, as indicated on the scale 26 on portion 19B in which portion 19A is restrained by a calibrated spring. Then a separate crimping tool (not shown) is applied to the portion 27 of the crimp 14 and crimps it onto the cable portion extending through aperture 24. Then the cable clamp 18 can be loosened, whereupon the tensioning tool can be removed from the cable and the cable is cut off at the abutment face 23, flush with face 23. The cable is secure to the bone.

Figure 2:
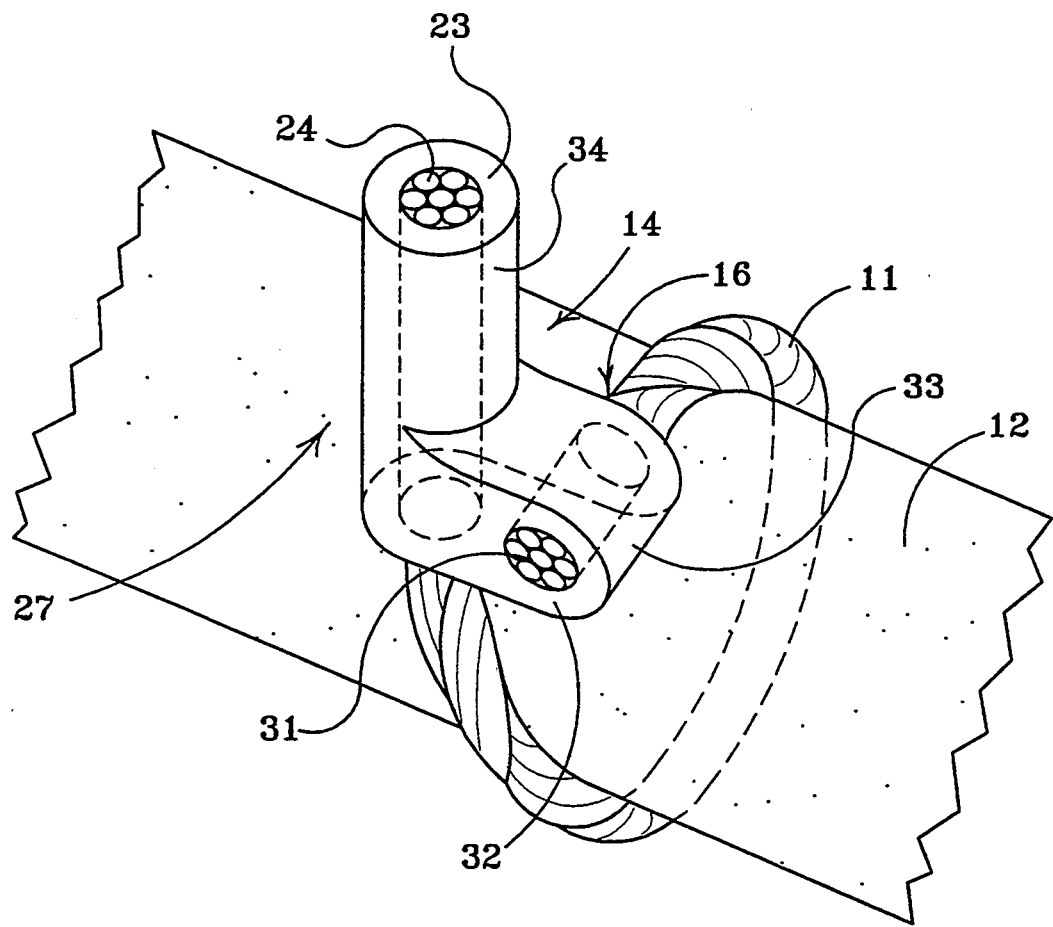
FIG. 2 is an enlarged fragmentary view of the attachment, when completed.

Referring more specifically now to FIG. 2, the one end 31 of the cable portion received in the base portion 32 of the crimp 14, is secured therein by swaging at 33 in a die press at the factory. After the cable has been wrapped around the bone and adequately tensioned, the column portion 27 is swaged as at 34 by a suitable crimping tool as are known in the art. The cable end received up through the longitudinal aperture 24 from the bottom 36 to the top abutment surface 23 is cold crimped by such a tool after the desired tension has been applied to the cable.

It should be understood, of course, that if it is desired to secure two bones within the loop of the cable, or one or more bones and spinal rods or other devices within the loop, that can be done in a similar manner.

As an example, the crimp member can be made from 316 LVM ASTM38F-138 stainless steel, annealed dead soft so that it can be easily swaged. The cable can be commercially pure titanium (CP Ti) ASTM F-67. The overall height from face 23 to face 36 in the illustrated example is 0.254 inches (6.45 mm). The overall width between the two parallel faces of the base portion 32 receiving the anchor end of the cable is, for example, 0.088 inches (2.23 mm).

Figure 3:
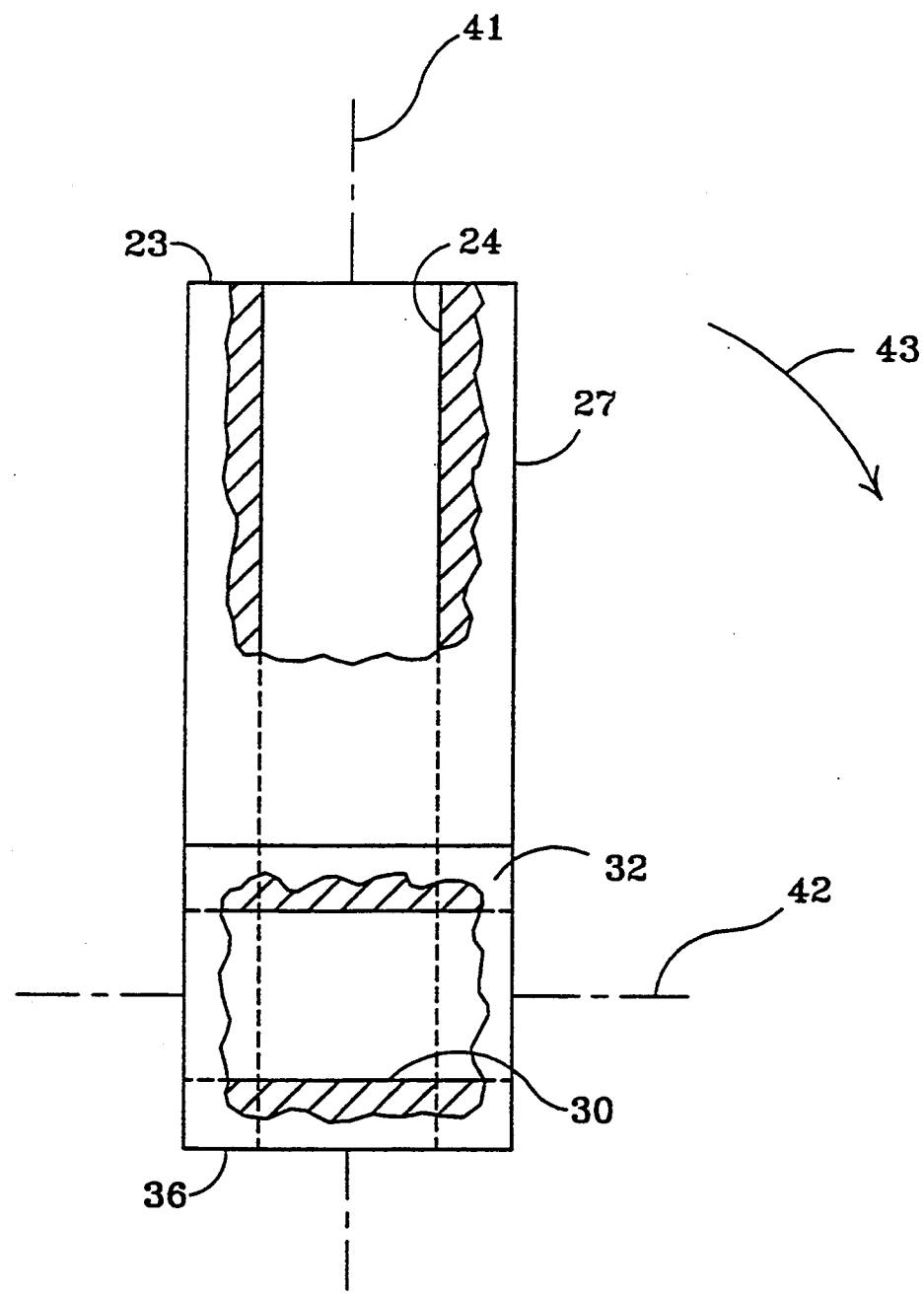
FIG. 3 is an enlarged elevational view of the crimp with portions broken out to show interior details.

As an example, where the cable anchoring aperture in the base portion 32 is cylindrical, the diameter may be 0.065 inches (1.65 mm). The same diameter would be applicable in the cylindrical aperture 24 of the column portion of the crimp. As is evident in FIG. 3, where portions of the crimp are broken away to show the two internal apertures 24 and 30, the longitudinally extending central axes of these apertures lie in planes which are parallel to each other and to the plane of the paper, and in planes 41 and 42 which are perpendicular to the plane of the paper. For some purposes, it is conceivable that, instead of the body portion 14 of the crimp member being specifically L-shaped as shown in FIGS. 1 and 2, it can be modified by rotating the plane 41 toward plane 42 in the direction of arrow 43 if it is desired to have a different orientation of the cable around the bone, particularly at the cable entrance face to the cable receiving aperture 24 of the on-site crimpable portion 27.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical cable assembly comprising:
   a crimp having first and second crimpable portions with first and second apertures therein, respectively;
   a cable having an opposite portion fixed in the first aperture in the crimp and an end portion receivable through the second aperture in the crimp;
   the cable being crimped in the second aperture at a location along the cable between the fixed end portion and the opposite end portion;
   the first aperture being separate from the second aperture;
   the apertures having longitudinally extending central axes in parallel planes;
   the axis of one of the apertures being perpendicular to a third plane containing the axis of the other aperture,
   the axis of the other aperture lying in the third plane.

2. The cable assembly of claim 1 and wherein:
   the crimp is made of stainless steel annealed dead soft; and
   the cable is made of multiple strands of commercially pure titanium.

3. A surgical cable assembly for encircling bone comprising:
   a generally L-shaped body for securing and maintaining the cable around said bone and having a base portion and a column portion,
   a multiple strand round metal cable having one end portion fixed in the base portion, and
   an aperture in the column portion sized to receive the other end of the cable therethrough.

4. The assembly of claim 3 and wherein:
   the one end portion is irreversibly fixed in the base portion.

5. The assembly of claim 3 and wherein:
   there is an aperture in the base portion,
   each of the apertures has a longitudinal axis,
   the aperture being separated from each other, and the axes of the apertures lying in two perpendicular planes.

6. The assembly of claim 5 and wherein:
   the one end portion is fixed in the aperture in the base portion,
   the cable extends from the one fixed end portion out of the body at the base portion and back into the body at an end of the first-mentioned aperture adjacent the base portion and up through the first-mentioned aperture to the top of the column portion.

* * * * *